United States Patent [19]

Long

[11] Patent Number: 5,172,587
[45] Date of Patent: Dec. 22, 1992

[54] PILE LOAD TESTING DEVICE

[75] Inventor: Erwin L. Long, Anchorage, Ak.

[73] Assignee: Arctic Foundations, Inc., Anchorage, Ak.

[21] Appl. No.: 668,777

[22] Filed: Mar. 13, 1991

[51] Int. Cl.$^5$ .................. G01N 33/24; G01N 3/08; G01N 3/42

[52] U.S. Cl. ................................. 73/84; 73/784

[58] Field of Search ........................... 73/784, 866, 84

[56] References Cited

U.S. PATENT DOCUMENTS

| | | | |
|---|---|---|---|
| 3,470,701 | 10/1969 | Turzillo | 73/84 X |
| 3,557,886 | 1/1971 | Cobbs | 73/784 X |
| 3,706,204 | 12/1972 | Long | 405/30 |
| 3,721,095 | 3/1973 | Chelminski | 405/232 |
| 3,797,257 | 3/1974 | Long | 405/232 |
| 3,946,601 | 3/1976 | Yizhaki | 73/84 |
| 3,950,954 | 4/1976 | Haug | 405/228 |
| 4,293,242 | 10/1981 | Merjan | 405/239 |
| 4,359,890 | 11/1982 | Coelus | 73/84 X |
| 4,614,110 | 9/1986 | Osterberg | 73/784 X |
| 4,770,030 | 9/1988 | Smith | 73/84 |
| 4,845,990 | 7/1989 | Bermingham | 73/786 X |

FOREIGN PATENT DOCUMENTS

| | | | |
|---|---|---|---|
| 1234300 | 10/1960 | France | 73/84 |
| 63778 | 5/1980 | Japan | 73/84 |
| 125402 | 5/1959 | U.S.S.R. | 73/84 |
| 614355 | 7/1978 | U.S.S.R. | 73/84 |
| 637481 | 12/1978 | U.S.S.R. | 73/84 |
| 687174 | 10/1979 | U.S.S.R. | 73/84 |

Primary Examiner—Tom Noland
Attorney, Agent, or Firm—Seed and Berry

[57] ABSTRACT

A device for testing the loading of a test pile extending downwardly into the ground. The device includes a reaction pile axially disposed inside the test pile and a reference pile axially disposed inside the reaction pile. The reaction pile extends further into the ground than the test pile and the reference pile extends further into the ground than the reaction pile. A loading device simultaneously exerts a downward force on the test pile and an upward reaction force on the reaction pile such that the test pile moves downwardly, and a laser distance measurement system, attached to the test pile and extending axially therewith, also moves downwardly. The laser distance measurement system resides in a test chamber defined by a shroud circumscribing the test device and secured to the top of the test pile so as to move downwardly therewith. Included in the distance measurement system is a first mirror disposed at the top of the reference pile, and a second mirror attached to the inside, top surface of the shroud. The two mirrors and laser system measure the rate of movement of the test pile with respect to the reference pile and the reaction pile with respect to the reference pile. The absolute rate of movement of the test pile is calculated by determining the difference between the rate of movement of reaction pile and the reference pile, and the rate of movement of the test pile and the reference pile.

19 Claims, 3 Drawing Sheets

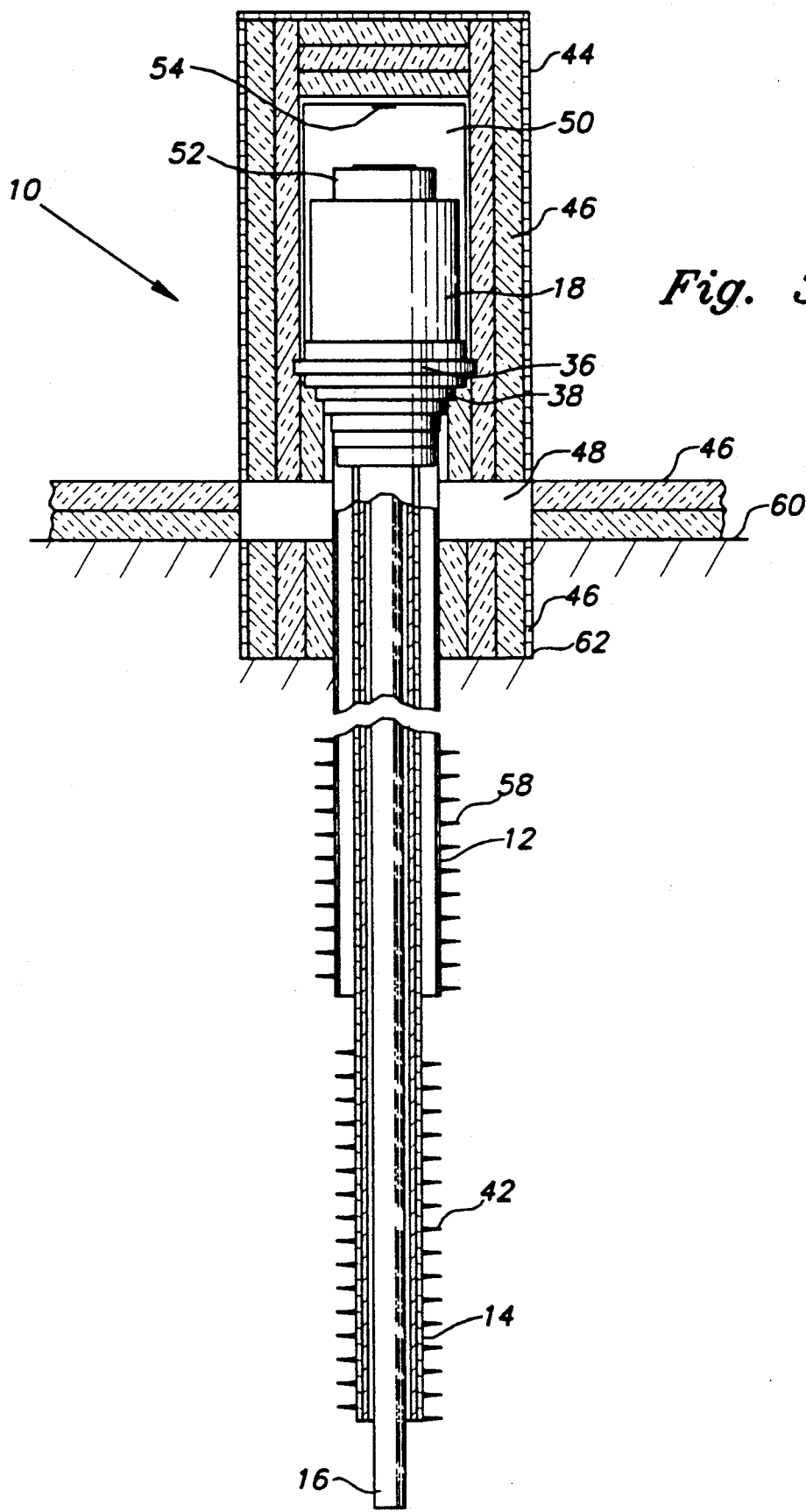

PILE LOAD TESTING DEVICE

TECHNICAL FIELD

This invention relates to a device for testing pile loading, and more particularly, to a device for measuring pile settlement in response to an axial load.

BACKGROUND OF THE INVENTION

Devices for testing the rate at which a pile settles in the ground, otherwise known as "creep," in response to an axial load are known in the art. There are two types of settlement readings. The first type is "adshear," or "adhesion shear," which is movement of the pipe relative to the soil which is in contact with the pile. When the soil is frozen, "adshear" is referred to as "adfreeze." The second type of settlement reading is "shear," which is movement of soil proximate the pile with respect to adjacent soil.

The purpose of testing the settlement rates of piles is to predict the estimated creep that can be expected over a 50-year period, for instance. An acceptable creep over a 50-year period may be ½ inch. The accuracy of the equipment used in testing the creep of a pile determines the required duration of a particular test in order to determine the expected creep rate. A 0.5-inch creep in 50 years corresponds to 0.01 inch in one year and 0.00019 inch in one week. Conventional equipment is theoretically capable of measuring 0.0001 inch of movement of a test pile. Thus, in order to obtain reliable results, it is often necessary to conduct a test over a period of weeks or even months in order to maximize the amount of movement. Moreover, temperature and pressure variations of the soil affect the accuracy of the test readings.

The conventional pile testing device includes a test pile which is either driven into the ground or is placed in an oversized hole and backfilled with either a soil/water slurry or a sand, cement grout. A pair of horizontally disposed reference beams are disposed on opposite sides of the test pile above the ground. The reference beams are supported at respective opposite ends by reference piles which are driven into the ground at a distance of not less than 8 feet from the test pile. In this manner, the creep movement of the test pile theoretically does not cause the reference piles and beams to move. Measures are taken in an attempt to insulate the reference beams from sun and wind exposure to further minimize movement of the reference beams. Measuring instrumentation is connected between each of the reference beams and the test pile to calculate the movement of the test pile. As noted above, the measuring equipment is capable of measuring 0.0001 inch. Finally, a load is applied on the top of the test pile, forcing the test pile into the ground such that the movement of the pile can be calculated over time, providing a predicted creep rate.

As can be understood from the above description of the conventional device, the problems associated with such a device are that the accuracy of the test procedure is poor and the test is relatively expensive to conduct. Most importantly, it is difficult to ensure that the reference beams will not be affected by, for instance, the movement of the test pile and environmental factors, such as air temperature and wind speed, as discussed above. Accordingly, since the measuring accuracy of the conventional test procedure is poor, the duration of the test must be relatively long in order to maximize the movement of the test pile to within a range that can be reasonably calculated to any degree of certainty. As noted above, tests lasting as long as four months are not uncommon. To accurately determine creep rates, a displacement measuring system capable of measuring microinches per hour is required

SUMMARY OF THE INVENTION

The present invention is designed to overcome the problems noted above. In a preferred embodiment, the present invention resides in a pile load testing device for testing the loading of a test pile extending downwardly into the ground, comprising a reaction pile axially disposed inside the test pile and extending further into the ground than the test pile, a reference pile disposed axially inside the reaction pile and extending further in the ground than both the test pile and the reaction pile, a loading device for simultaneously exerting a downward force on the test pile and an upward reaction force on the reaction pile such that the test pile moves downwardly, and a measuring device for detecting the rate at which the test pile moves downwardly. An insulated shroud circumscribes the testing device and is secured to the top of the test pile so as to move downwardly therewith. The shroud is designed to insulate a test chamber in the interior of the shroud so as to permit the temperature and pressure to be controlled, and to shield the test chamber from the wind.

The measuring device preferably includes a laser secured to the top of the reaction pile and extending axially with respect thereto, a first mirror secured to the top of the reference pile and a second mirror secured to the inside, top surface of the shroud, each of the mirrors being in axial alignment with the laser and being disposed on opposite ends thereof. To determine the amount of movement between the reaction pile and the reference pile, a laser beam, emitted from one end of the laser, is reflected off the first mirror. Correspondingly, to determine the amount of movement between the reaction pile and the test pile, a second beam, emitted from the opposite end of the laser, is reflected off the second mirror. In this manner, the absolute rate of movement of the test pile is calculated by determining the difference between the rate of movement of the reaction pile with respect to the reference pile, and the rate of movement of the reaction pile with respect to the test pile.

BRIEF DESCRIPTION OF THE DRAWINGS

FIG. 3 is a side view of the pile load testing device, according to a second preferred embodiment of the invention.

DETAILED DESCRIPTION OF THE INVENTION

Figure 1:
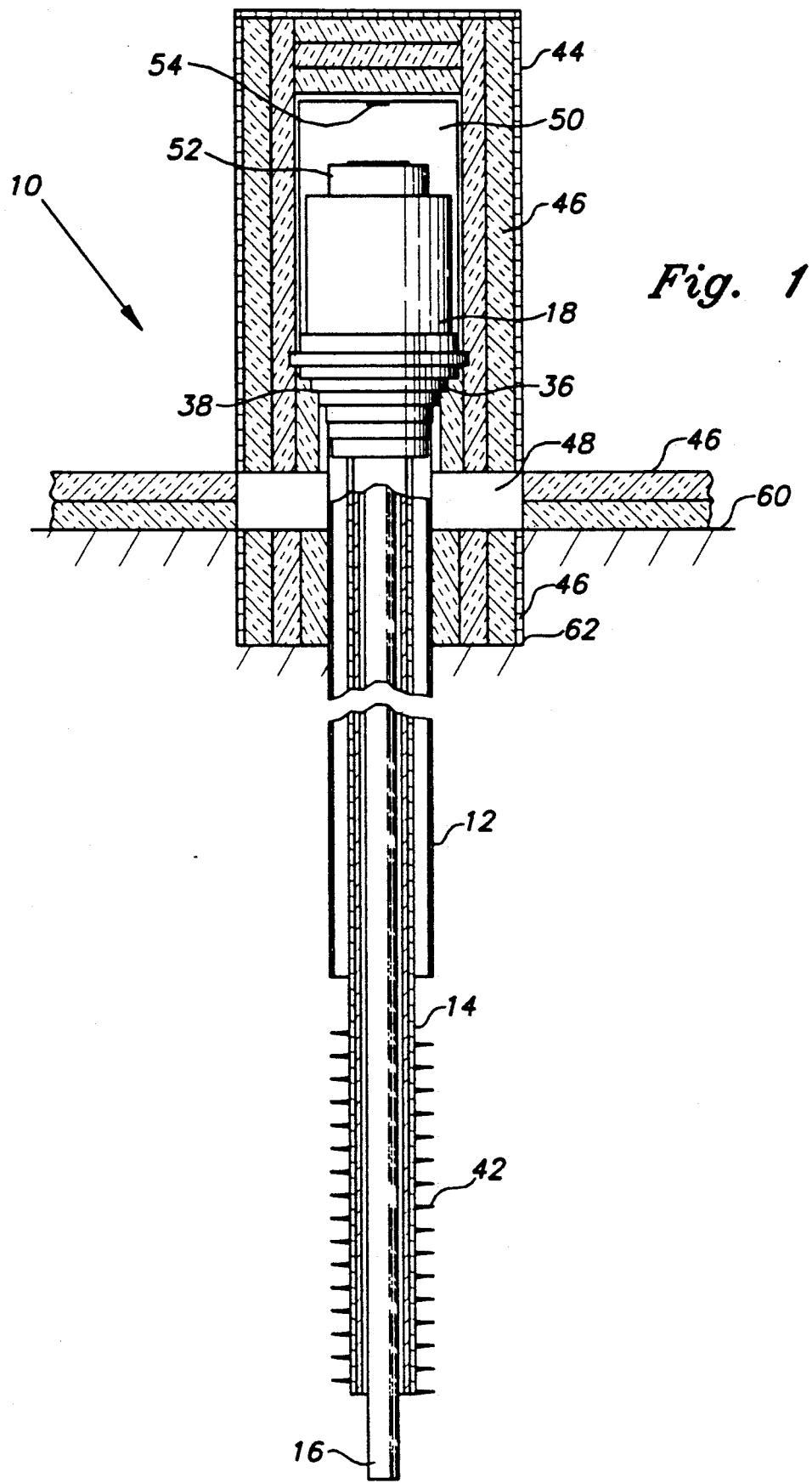
FIG. 1 is a side view of the pile load testing device, according to a first preferred embodiment of the present invention.
Figure 2:
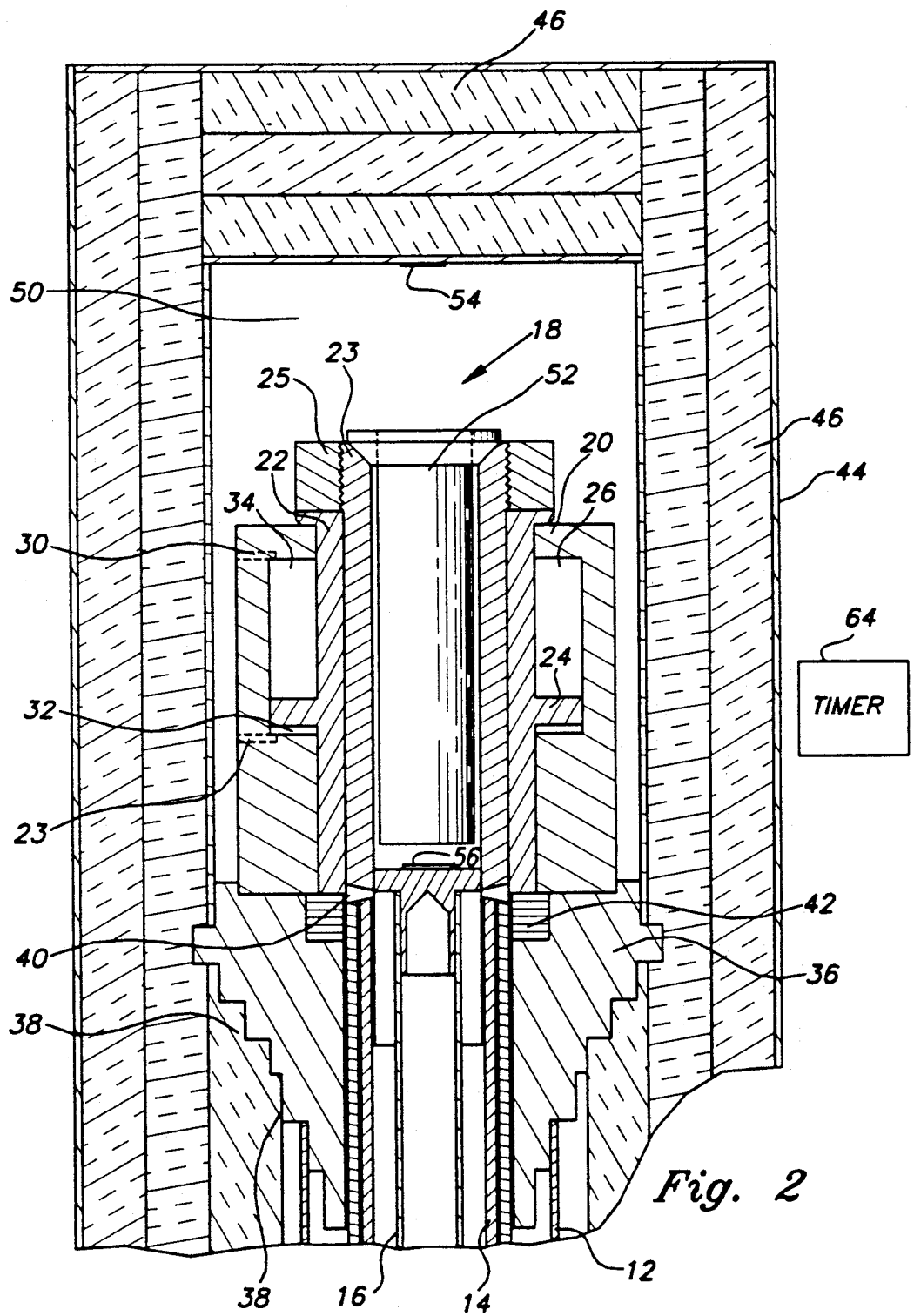
FIG. 2 is a detailed view of the loading device of the FIG. 1 embodiment.

Preferred embodiments of the present invention are illustrated in FIGS. 1-3. Referring to FIG. 1, the pile load testing device 10 includes a test pile 12, reaction pile 14 and reference pile 16 concentrically disposed with respect to one another and extending into the ground. In particular, the reference pile 16 is concentrically disposed inside the reaction pile 14 which is concentrically disposed inside the test pile 12. A loading device 18 is provided for simultaneously exerting a downward force on the test pile 12 and an upward force on the reaction pile 14. No force is applied to the reference pile 16. As is described in greater detail below, the creep rate of the test pile is calculated by comparing the rate of movement between the test pile 12 and the reaction pile 14 with the rate of movement between the reaction pile 14 and the reference pile 16.

FIG. 2 is a detailed view of the loading device 18. Referring thereto, the loading device includes a cylinder body 20 having a hollow ram 22 slidably disposed therein. Specifically, the hollow ram 22 includes a radially outwardly projecting ring 24 which is slidably disposed in a compression cylinder 26 defined by the cylinder body 20. A sleeve 23 is secured inside the ram 22 as illustrated in FIG. 2. The top portion of sleeve 23 has external threads for receiving a nut 25 and the bottom of the sleeve is welded to the reaction pile 14 at weld 40. Hydraulic ports 28, 30 are provided in the cylinder body 20 respectively communicating with opposing chambers 32, 34. In operation, hydraulic pressure is applied to chamber 32 via port 28 forcing the ram 22 in the upward direction and the cylinder body 20 in the downward direction, as explained in greater detail below. The upward force on the ram 22 is transmitted to the reaction pile 14 through the sleeve 23.

Disposed between the test pile 12 and the cylinder body 20 is a compression pile cap 36 which transfers the downward force from the cylinder body 20 to the test pile 12. The pile cap 36 is substantially conical in shape having a bottom portion comprising a plurality of stepped annular portions 38 having outer diameters corresponding to the inner diameters of standard test piles such that the pile cap can engage test piles of various standard diameters.

Referring again to FIG. 1, as noted above, the reference pile 16 is slidably disposed inside the reaction pile 14. The reference pile 16 is sufficiently long to extend deep into the ground to an extent necessary to ensure that the reference pile 16 remains stationary during the test procedure, and is not affected by movement of the test pile and the reaction pile. The reaction pile 14 is shorter than the reference pile 16 but longer that the test pile 12, as illustrated. In this manner, each of the piles is surrounded by ground soil. As noted above, the function of the reaction pile 14 is to oppose the downward force exerted on the test pile 12. It is desirable to minimize the amount of upward movement of the reaction pile. To accomplish this, the reaction pile 14 has spiralled securing blades 42 circumscribing the bottom portion thereof. The blades 42 serve to increase the amount of friction between the soil and the reaction pile 14 such that when the loading device 18 exerts an upward force on the reaction pile, the movement of the reaction pile is minimized.

As noted above, variations in temperature and pressure can have adverse effects on the test results. To overcome this problem, as illustrated in FIGS. 1 and 2, a shroud 44 is provided for covering the loading device 18, so as to define a test chamber 50 in which temperature and pressure can be controlled. The shroud 44 is secured to the outer circumference of the pile cap 36 such that the shroud can move downwardly with the pile cap 36 and test pile 12. Insulation 46 is provided on the interior surfaces of the shroud as well as along the top surface of the ground 60. Additionally, insulation is provided between the top surface of the ground 60 and the top of the test pile surface 62. A space 48 is provided between the bottom of the shroud 44 and the top of the insulation 46 proximate the test pile 12 to permit the shroud to move downwardly, as explained above. The insulation is designed to allow the temperature and pressure of the test chamber 50 to be controlled. Referring to FIG. 2, to regulate the temperature of the test chamber 50, a thermoelectric heat/cool device 42 is provided in a recess in the pile cap 36 and is in thermal contact with the pile cap 36, the reaction pile 14 and the ram 22. As is described in more detail below, a laser disposed in the test chamber is used to measure the movement of the test pile. Since the laser is substantially circumscribed by the ram 22, the temperature of the laser is also controlled.

As noted above, the movement of the reaction pile 14 and test pile 12 is measured with a laser interferometry system, described as follows. Suitable laser interferometry systems are model nos. HP5527A, HP5528A, VMEBUS and 5501A, manufactured by Hewlett Packard. Referring again to FIG. 2, a laser system 52 is secured to the inside of the sleeve 23 with the longitudinal axis of the laser system concentric to the longitudinal axis of the sleeve. The laser system is capable of emitting a beam from opposite longitudinal ends thereof. A first mirror 54 is secured to the shroud which, as described above, is secured to the pile cap 36 to which the test pile is secured. Accordingly, relative movement, $X_{tr}$, between the test pile 12 and the reaction pile 14 is measured by reflecting a beam off the first mirror 54. A second mirror 56 is secured to the top of the reference pile 16, as illustrated. Since the laser system 52 is secured to the reaction pile 14, relative movement, $X_{rr}$, between the reference pile 16 and the reaction pile 14 is measured by reflecting a laser beam emitted from the bottom end of the laser off the mirror 56. Thus, the absolute movement, $X_t$ of the test pile 12 is calculated as follows:

$$X_t = X_{tr} - X_{rr}.$$

By conducting this test over a known period of time, a predicted creep rate is calculated. A timer 64 is used to measure the known period of time. The timer 64 may be any one of many suitable forms of timer or clock well-known to those skilled in the art.

As noted above, there are two types of creep that can be measured "adshear" corresponding to the movement of the pipe relative to the soil contacting the pipe, and "shear" corresponding to the movement of soil proximate the pile with respect to the adjacent peripheral soil. In the preferred embodiments described herein, the configuration of the bottom portion of the test pile 12 varies depending the type of creep being tested. Referring to FIG. 1, when testing for "adshear" the bottom portion of the test pipe 12 is tubular in shape such that the pipe can slide downwardly relative to the soil in contact therewith. On the other hand, as illustrated in FIG. 3, when testing for "shear," the bottom portion of the test pipe 12 has a spiralled securing blade 58 similar to the securing blade 42 discussed above in regard to the reaction pile 14. The purpose of the securing blade 58 on the test pile is to prevent the test pile 12 from moving relative to the soil in contact therewith so as to cause the immediately adjacent soil to move relative to the peripheral soil. In this manner, the "shear" of the soil is measured.

As can be seen from the foregoing, the pile load testing device of the invention is capable of measuring pile creep much more precisely than the conventional test device.

It will be appreciated that, although specific embodiments of the invention have been described herein for purposes of illustration, various modifications may be made without departing from the spirit and scope of the invention. Accordingly, the invention is not limited except as by the appended claims.

What is claimed:

1. A pile load testing device for testing the loading of a test pile extending downwardly into the ground, comprising:
    a reaction pile axially disposed inside said test pile and extending downwardly into the ground;
    means for simultaneously exerting a downward force on said test pile and an upward force on said reaction pile such that said test pile moves downwardly;
    means for detecting the test rate at which said test pile moves downwardly with respect to the ground.

2. The testing device of claim wherein said detecting means comprises:
    a reference pile disposed proximate said reaction pile and said test pile and extending into the ground, said reference pile remaining stationary with respect to said ground;
    second means for measuring a second rate at which said reaction pile moves upwardly with respect to said reference pile; and
    third means for measuring a third rate at which said test pile moves downwardly with respect to said reaction pile, wherein said test rate at which said test pile moves downwardly equals the difference between said second and third rates.

3. The testing device of claim 2 wherein said reference pile is axially disposed inside said reaction pile.

4. The testing device of claim 3 wherein said second measuring means comprises a laser axially secured inside said reaction pile and being movable therewith and a first mirror secured to said reference pile in axial alignment with said laser and opposing one end thereof such that a beam emitted by said laser can be reflected off said first mirror to determine the amount of movement of said reaction pile with respect to said reference pile.

5. The testing device of claim 4 wherein said third measuring means comprises said laser a second mirror connected to said test pile and in axial alignment with said laser and opposing an opposite end thereof such that a beam emitted by said opposite end of said laser can be reflected off said second mirror to determine the amount of movement between said reaction pile and said test pile.

6. The testing device of claim 3 wherein said reaction pile is longer than said test such that said reaction pile extends deeper into said ground than said test pile.

7. The testing device of claim 6 wherein said reference pile is longer than both said test pile and said reaction pile such that said reference pile extends deeper into said ground than said test pile and said reaction pile.

8. The testing device of claim 3, further comprising means for limiting said second rate at which said reaction pile is moved upwardly with respect to said reaction pile.

9. The testing device of claim 8 wherein said limiting means comprises a spiralled securing blade circumscribing said reaction pile, said securing blade increasing the friction between said reaction pile and soil proximate thereto.

10. The testing device of claim 3, further comprising soil retaining means for causing said test pile to retain soil in contact therewith such that when said test pile moves downwardly, such downward movement causing a shearing action between adjacent soil rather than between said test pile and soil in contact therewith.

11. The testing device of claim 10 wherein said soil retaining means comprises a spiralled securing blade circumscribing said test pile, said securing blade increasing the friction between said test pile and soil proximate thereto.

12. The testing device of claim 3, further comprising means for testing load piles of various standard diameters.

13. The testing device of claim 1, further comprising an insulated shroud covering said test pile and said detecting means and being secured to said test pile to define a test chamber in the interior thereof which is insulated from the atmosphere.

14. The testing device of claim 13, further comprising temperature controlling means for controlling the temperature of said test chamber.

15. The testing device of claim 14 wherein said temperature controlling means comprises a thermoelectric device circumscribing said reaction pile.

16. A pile load testing device for testing the loading of a test pile extending into the ground, comprising:
    a reference pile axially disposed inside said test pile and extending downwardly into the ground;
    force exerting means for exerting a downward force on said test pile such that said test pile moves downwardly; and
    means for detecting the test rate at which said test pile moves downwardly with respect to the ground.

17. The testing device of claim 16, wherein said force exerting means comprises a reaction pile and a loading means, said bonding means exerting a downward force on said test pile and an opposing upward force on said reaction pile.

18. The testing device of claim 17 wherein said reaction pile is axially disposed in said test pile.

19. The testing device of claim 18 wherein said reference pile is axially disposed in said reaction pile.

* * * * *

UNITED STATES PATENT AND TRADEMARK OFFICE
CERTIFICATE OF CORRECTION

PATENT NO. : 5,172,587
DATED : December 22, 1992
INVENTOR(S) : Erwin L. Long

It is certified that error appears in the above-indentified patent and that said Letters Patent is hereby corrected as shown below:

In column five, claim two, line 23, after "claim" and before "wherein", please insert --1--.

In column five, claim five, line 48, after "laser" and before "a second", please insert --and--.

In column five, claim six, line 56, after "said test" and before "such that", please insert --pile--.

In column six, claim 17, line 50, please delete "bonding" and substitute therefor --loading--.

Signed and Sealed this

Fifteenth Day of February, 1994

Attest:

BRUCE LEHMAN

Attesting Officer

Commissioner of Patents and Trademarks